United States Patent [19]

Schwartz

[11] 4,235,594
[45] Nov. 25, 1980

[54] PREFABRICATED BITE BLOCK STRUCTURE

[76] Inventor: Robert Schwartz, 1271 Westfield Ave., Rahway, N.J. 07065

[21] Appl. No.: 25,856

[22] Filed: Apr. 2, 1979

[51] Int. Cl.³ ............................................. A61C 19/04
[52] U.S. Cl. ...................................... 433/68; 433/213
[58] Field of Search ...................... 433/68, 69, 71, 72, 433/37, 68

[56] References Cited

U.S. PATENT DOCUMENTS

| | | | |
|---|---|---|---|
| 2,618,853 | 11/1952 | Singer et al. | 433/69 |
| 3,619,903 | 11/1971 | Schreinemaker | 433/37 |
| 3,690,004 | 12/1972 | Frush | 433/37 |
| 3,727,309 | 4/1973 | Huey | 433/171 |

Primary Examiner—Robert Peshock

[57] ABSTRACT

A prefabricated bite block structure is provided comprising a maxillary tray and a mandibular tray, each formed from a heat-deformable thermoplastic material. The maxillary tray generally corresponds to the maxillary alveolar ridge and palate of the human anatomy and is adapted to be positioned on the maxillary alveolar ridge. The mandibular tray generally corresponds to the mandibular ridge, retromolar pad areas, mucobuccal fold areas and mucolingual fold areas of the human mandible and is adapted to be positioned on the mandibular alveolar ridge. The maxillary and mandibular trays each have protrusions terminating in a flat, planar occlusal surface that corresponds at least to the area occupied by the canines, premolars and first molars. The planar occlusal surfaces of the trays correspond approximately to the plane of occlusion as defined by certain anatomical landmarks. The occlusal surfaces of the maxillary and/or mandibular trays are also adapted to receive and retain shim members which serve to increase, to the extent of the thickness of the shim member, the vertical dimension of the protruding occlusal surfaces of the maxillary and mandibular trays.

5 Claims, 3 Drawing Figures

PREFABRICATED BITE BLOCK STRUCTURE

BACKGROUND OF THE INVENTION

This invention relates to a prefabricated bite block structure. More particularly, this invention is concerned with a prefabricated bite block structure comprising maxillary and mandibular tray members having occlusal surfaces that correspond approximately to the dental plane of occlusion as defined by certain anatomical landmarks and which are adapted to be altered by the addition of shim members to vary the vertical dimension of the bite block structure.

The use of bite blocks in full and partial denture construction is an old and accepted dental discipline. Bite blocks have been employed by practitioners to aid in the formation of fixed and removable prosthesis. Using bite blocks the practitioner can establish vertical dimension, plane of occlusion and a centric position. Bite blocks also assist in establishing inter-arch relationship of the occlusion, the establishment of inter-arch relationship of the restorations and the existing dentition of the patient and setting of esthetic guidelines such as labial drape, high and low lip line, smile line, mid-line and cuspid points. Typically, bite blocks are custom formed from casts made of the patient's dental anatomy.

Using conventional practice, the practitioner takes a preliminary impression of the maxillary and/or mandibular anatomy from which casts are formed. A tray is then formed on top of the cast using thermoplastic, heat deformable materials. These preliminary trays are then trimmed as required to seat comfortably on the patient's anatomy and then possibly border molded with a heat malleable compound, such as wax. These preliminary trays are then employed to hold and retain impression materials from which a final impression of the patient's anatomy is secured. From these final impressions are formed final casts from which another set of trays are formed as described above. Wax is then luted to the occlusal surfaces of the trays and the semicompleted blocks placed in the patient's mouth. Additional wax is added to the occlusal surfaces as necessary to establish the desired vertical dimension, plane of occlusion, etc. The final bite blocks are then employed as models in the ultimate fabrication of the patient's prosthesis.

Using the aforementioned conventional technique occupies a great deal of patient and practitioner time. Frequently, a number of visits are required before a final bite block system can be completed.

SUMMARY OF THE INVENTION

It has now been found that the time involved in the preparation of bite blocks employed in the fabrication of dental prosthesis can be diminished by the use of a prefabricated bite block system of the present invention. The bite block structure comprises a prefabricated maxillary tray 1 and a prefabricated mandibular tray 2, each having an inner and outer surface terminating at a flange portion; and shim members 40 that are adapted to be removably located on the occlusal surfaces of the maxillary tray 1 and/or mandibular tray 2. The maxillary and mandibular trays are formed from a heat-deformable material, preferably a thermoplastic composition. The inner surface of the maxillary tray 1 corresponds to the human maxillary alveolar ridge and palate and is adapted to be positioned on the maxillary alveolar ridge. The inner surface of the mandibular tray 2 corresponds to the mandibular ridge, retromolar pad areas, mucobuccal fold area and mucolingual fold area of the human mandible and is designed to be positioned on the mandibular alveolar ridge. The outer surfaces of the maxillary and mandibular trays are formed having protrusions terminating as flat, planar occlusal surfaces that correspond at least to the areas occupied by the canines, premolars and first molars of normal human dentition. The planar occlusal surface of the maxillary tray, when the tray is positioned on the maxillary alveolar ridge of the patient, is substantially parallel to the plane defined by the hammular notches and the center of the palatine papilla. The planar occlusal surface of the mandibular tray, when positioned on the patient's mandibular alveolar ridge, is substantially parallel to the plane defined by the centers of the retromolar pads and a point about 5 to 20 millimeters, preferably about 15 millimeters, above the intersection of the patient's mandible midline with the mucobuccal fold.

The elements of the present invention will become more apparent upon reading the following detailed description of the invention.

DETAILED DESCRIPTION OF THE INVENTION

Figure 1:
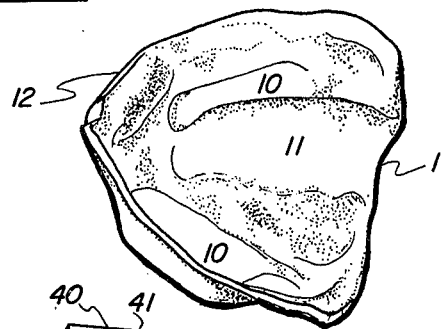
FIG. 1 is a top view of the maxillary tray 1 of the prefabricated bite block structure.
Figure 2:
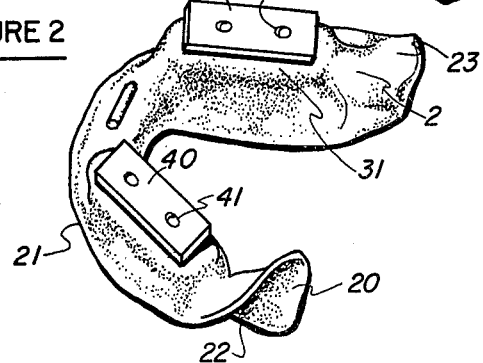
FIG. 2 is a perspective illustration of the mandibular tray 2 of the bite block structure with shim members 40 in place on the occlusal surfaces.
Figure 3:
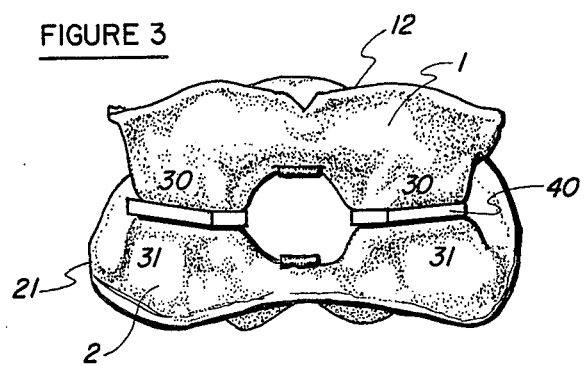
FIG. 3 is a perspective front view of the complete pre-fabricated bite block structure with shim members 40 in place on the occlusal surfaces of the mandibular tray 2.

The maxillary tray of FIG. 1 and the mandibular tray of FIG. 2 each have inner and outer surfaces and, as noted previously, are preferably formed from a heat deformable material, such as thermoplastic olefin polymers. The inner surface of the maxillary tray 1 corresponds to the maxillary alveolar ridge 10 and palate 11 and is adapted to be positioned on the maxillary alveolar ridge. The inner surface of the mandibular tray corresponds to the mandibular ridge (not shown), retromolar pad areas 20, mucobuccal fold area 21 and mucolingual fold area 22, and is adapted to be positioned on the mandibular alveolar ridge. As shown in FIGS. 1 and 2, the outer surfaces of both the maxillary tray 1 and the mandibular tray 2 have protrusions terminating as flat, planar occlusal surfaces that correspond at least to the area occupied by the canines, premolars and first molar areas of the human dentition (protrusions designated as 30 and 31 in the Figure). It should be recognized that the occlusal surfaces may be expanded from the minimum area mentioned above to include areas normally occupied by other elements of the human dentition. The planar occlusal surface of the maxillary tray (bottommost portion of the maxillary tray protrusion), when the tray is in position on the maxillary alveolar ridge, is substantially parallel to the plane defined by the hammular notches and the center of the palatine papilla. As a general proposition, the occlusal surface plane of the maxillary bite block lies in a plane about 10 to 25 millimeters vertically, preferably about 20 millimeters, below the anterior-most portion of the flange 12 (upper periphery) of the maxillary tray.

The planar occlusal surface of the mandibular tray (uppermost portion of the mandibular tray protrusion), when positioned on the mandibular alveolar ridge, is substantially parallel to the plane defined by the centers 23 of the retromolar pads (laterally and longitudinally) and a point about 5 to 20, preferably about 15 millimeters above the intersection of the patient's mandible midline with the mucobuccal fold. In typical human dentition, the occlusal surface of the mandibular tray 2 lies in a plane about 10 to 26, preferably about 18 millimeters vertically above the anterior-most portion of the flange (corresponds to mucobuccal fold areas 21) of the mandibular tray. The archwidth of the prefabricated mandibular trays preferably corresponds to distances described in standard arch indices such as Hawley arch charts, Pont's index, etc.

The tray members are adapted to receive and removably retain shim members 40 on the occlusal surfaces. The shim members may be of varying vertical thicknesses and serve to provide additional vertical dimension in the bite block structure. The shim members 40 are preferably of a length substantially equal to the length of the occlusal surfaces and may be positioned on either or both of the maxillary and mandibular trays. The mechanical arrangement used to retain the shims upon the occlusal surfaces is not critical. For example, the shim members 40 may be provided with plug elements which are adapted to be placed within corresponding hole elements in the occlusal surfaces and the shim members simply retained on the occlusal surfaces by a force fit.

In use, the maxillary tray 1 and mandibular tray 2 of appropriate arch widths are placed in the patient's mouth upon the alveolar ridges. Some trimming of the flanges of the trays may be required to secure a comfortable fit. Thereafter shim members 40 of appropriate thickness are placed upon the occlusal surfaces of the maxillary and/or mandibular trays to secure the approximate vertical dimension. The maxillary tray 1 is then removed from the patient's mouth and a typical impression material placed within the inner surface of the tray and the tray replaced on the maxillary alveolar ridge of the patient. The maxillary tray 1 is seated into place by having the patient bite down upon the lower tray with the maxillary tray in place. Thereafter, the lower or mandibular tray 2 is removed from the patient's mouth, partially filled with a standard impression material and replaced upon the mandibular alveolar ridge. The patient then bites down to seat the mandibular tray 2 into position. At this point, additional shim elements may be added to the trays or the existing shim elements replaced to secure the desired vertical dimension. Once the desired vertical dimension is achieved, a thin layer of wax is spread over the occlusal surface of trays 1 and/or 2 or over the exposed surface of the shim members 40 and the patient then bites down upon the same to force the wax against the occlusal surfaces of the trays or shim members 40 placed thereon. This action serves to force wax onto the occlusal surfaces or shim elements located thereon to establish the relationship between the upper and lower trays when the mouth is in a closed relationship. Preferably, the occlusal surfaces or outer exposed surfaces of shim elements 40 located thereon are provided with shallow grooves or holes (see holes 41 in the exposed surfaces of shim members 40) into which the wax is forced. The presence of such grooves or holes or other locating indentation cause the formation of a pattern on the wax which can be used to reestablish the relationship between the upper tray 1 to the lower tray 2 after the same are removed from the mouth. The finished bite blocks are then employed to manufacture the patient's prosthesis as per usual practice.

What is claimed is:
1. A prefabricated bite block structure comprising:
  (a) a maxillary tray and a mandibular tray each having an inner and outer surface terminating at a flange portion, said trays formed from a heat-deformable material; the inner surface of the maxillary tray corresponding to the maxillary alveolar ridge and palate and adapted to be positioned on the maxillary alveolar ridge; the inner surface of the mandibular tray corresponding to the mandibular ridge, retromolar pad areas, mucobuccal fold area and mucolingual fold area and adapted to be positioned on the mandibular alveolar ridge; the outer surface of the maxillary and mandibular trays having protrusions terminating as flat, planar occlusal surfaces that correspond at least to the area occupied by the canines, premolar and first molars; the planar occlusal surface of the maxillary tray, when said tray is positioned on the maxillary alveolar ridge, being substantially parallel to the plane defined by the hammular notches and the center of the palatine papilla; and the planar occlusal surface of the mandibular tray when positioned on the mandibular alveolar ridge, being substantially parallel to the plane defined by the centers of the retromolar pads and point about 5 to 20 millimeters above the intersection of the mandible midline with the mucobuccal fold; and
  (b) shim members adapted to be removably located on said occlusal surface of the maxillary and/or mandibular trays.

2. The article of claim 1 wherein the vertical distance between the anterior-most portion of the flange of the maxillary tray and the planar occlusal surface of said tray varies from about 10 to 25 millimeters.

3. The article of claim 2 wherein said vertical distance is about 20 millimeters.

4. The article of claim 1 wherein the vertical distance between the anterior-most portion of the flange of the mandibular tray and the planar occlusal surface of said tray varies from about 10 to 26 millimeters.

5. The article of claim 4 wherein said distance is about 18 millimeters.

* * * * *